US010201910B2

(12) United States Patent
Humphrey et al.

(10) Patent No.: US 10,201,910 B2
(45) Date of Patent: Feb. 12, 2019

(54) WOOD PRESERVATIVE FORMULATION

(71) Applicant: ARCH WOOD PROTECTION PTY LTD, Tullamarine, Victoria (AU)

(72) Inventors: David Humphrey, Tullamarine (AU); Brett Skewes, Tullamarine (AU); Shane McFarling, Tullamarine (AU)

(73) Assignee: Arch Wood Protection Pty Ltd, Tullamarine, Victoria (AU)

( * ) Notice: Subject to any disclaimer, the term of this patent is extended or adjusted under 35 U.S.C. 154(b) by 0 days.

(21) Appl. No.: 15/527,755

(22) PCT Filed: Nov. 24, 2015

(86) PCT No.: PCT/AU2015/000715
§ 371 (c)(1),
(2) Date: May 18, 2017

(87) PCT Pub. No.: WO2016/081981
PCT Pub. Date: Jun. 2, 2016

(65) Prior Publication Data
US 2017/0320230 A1    Nov. 9, 2017

(30) Foreign Application Priority Data
Nov. 24, 2014    (AU) .............................. 2014904750

(51) Int. Cl.
| | | |
|---|---|---|
| *B27K 3/36* | (2006.01) | |
| *A01N 25/02* | (2006.01) | |
| *B27K 3/22* | (2006.01) | |
| *B27K 3/50* | (2006.01) | |
| *C09D 5/14* | (2006.01) | |
| *A01N 43/653* | (2006.01) | |
| *A01N 53/00* | (2006.01) | |
| *A01N 59/20* | (2006.01) | |
| *B27K 3/08* | (2006.01) | |
| *B27K 3/16* | (2006.01) | |
| *B27K 3/20* | (2006.01) | |
| *B27K 3/34* | (2006.01) | |
| *B27K 3/52* | (2006.01) | |

(52) U.S. Cl.
CPC ................ *B27K 3/36* (2013.01); *A01N 25/02* (2013.01); *A01N 43/653* (2013.01); *A01N 53/00* (2013.01); *A01N 59/20* (2013.01); *B27K 3/08* (2013.01); *B27K 3/16* (2013.01); *B27K 3/20* (2013.01); *B27K 3/22* (2013.01); *B27K 3/343* (2013.01); *B27K 3/50* (2013.01); *B27K 3/52* (2013.01); *C09D 5/14* (2013.01)

(58) Field of Classification Search
CPC ... B27K 3/36; B27K 3/50; B27K 3/22; A01N 25/02; A01N 43/653; A01N 53/00; A01N 59/20; C09D 5/14
USPC ....................................................... 428/541
See application file for complete search history.

(56) References Cited

U.S. PATENT DOCUMENTS 5,665,432 A * 9/1997 Kuwazuru ........... A01N 43/653
252/380
2014/0329014 A1    11/2014 Cobham

FOREIGN PATENT DOCUMENTS

| AU | 2008205451 | | 9/2008 |
|---|---|---|---|
| EP | 1679166 | | 4/2012 |
| JP | 2005-120081 | | 5/2005 |
| JP | 40-22898 | B2 | 12/2007 |
| JP | 4022898 | * | 12/2007 |
| WO | WO 2000/066668 | | 11/2000 |
| WO | WO2009/129587 | * | 10/2009 |
| WO | WO 2009/129587 | | 10/2009 |
| WO | WO2013/090995 | * | 6/2013 |
| WO | WO 2013/090995 | | 6/2013 |

OTHER PUBLICATIONS

Teknos A/S , Gori vac TH92ic Concentrate—Technical Data Sheet Mar. 2014.*
Teknos A/S Resistol 6109 Data Sheet, Feb. 16, 2005.*
TEKNOS A/S, Gori vac TH92ic, Concentrate Technical Data Sheet, Aug. 15, 2013, 2 pages.
TEKNOS A/S, Resistol, 6109 Data Sheet, dated Feb. 16, 2005, 2 pages.
Arch Wood Protection, Material Safety Information: H3 LOSP Azole Treated Wood Products, Dec. 2007, 4 pages.
Siraa, et al., The International Research Group on Wood Protection: Section 3—Wood Protecting Chemicals: Methylene chloride compared with white spirit as a treatment solvent for wood preservation; 44th Meeting, Stockholm; Jun. 2013, 8 pages.
PCT/AU2015/000715/ International Search Report, dated Feb. 18, 2016.

* cited by examiner

*Primary Examiner* — Leszek B Kiliman
(74) *Attorney, Agent, or Firm* — Dority & Manning, P.A.

(57) ABSTRACT

According to the present invention there is provided the use of one or more low aromatic or substantially low aromatic solvents as a carrier, for efficacious use within a preservative formulation for treating wood or other cellulosic species. The invention also provides for a wood preservative formulation comprising such a carrier. In an embodiment, the carrier is selected from the commercially-available range of Exxsol® D and Isopar® fluids.

23 Claims, 4 Drawing Sheets

WOOD PRESERVATIVE FORMULATION

RELATED APPLICATION

This application claims priority from PCT/AU2015/000715, filed on Nov. 24, 2015 and Australian patent application 2014904750, filed on Nov. 24, 2014. The content of the priority applications are incorporated herein by reference in their entirety.

FIELD OF THE INVENTION

The present invention relates to the treatment of wood products and other cellulosic formulations with a preservative formulation. More specifically, the invention relates to developments in respect of carriers—agents that facilitate the penetration of the preservative/s into the wood. Although the invention will be described hereinafter with reference to this application, it will be appreciated that it is not limited to this particular field of use.

BACKGROUND OF THE INVENTION

Any discussion of the prior art throughout the specification should in no way be considered as an admission that such prior art is widely known or forms part of the common general knowledge in the field.

Wood is a staple construction formulation used throughout the world. However, it is prone to degradation from elements including the natural environment, weather events, insects, rot and fire. Accordingly, a range of chemical treatments has been developed to improve the durability and working lifetime of wooden structures.

To treat and prevent infestations, timber is often impregnated with a preservative such as a fungicide or insecticide. The preservative is typically present in a carrier, with the mixture being applied to the surface of the timber, for example by dipping, spraying, brushing or pressure treatment, such that the carrier and preservative are absorbed in to the timber. As such, the treatment of timber with preservative compounds involves the introduction of stable chemicals into the cellular structure of the timber. This, in turn, protects the timber from hazards such as fungi, insects and other wood-destroying organisms. Preservative treatments may also include the introduction of chemicals that improve resistance to degradation by fire.

In Australia, the treatment of timber is governed by the Australian standard "AS 1604-2012". Hazard Class H3 is defined as being for protection against "moderate fungal decay and termite hazard" with examples of end uses being decking, fascia, cladding, window reveals, and exterior structure timber. The timber is exposed to the weather or not fully protected. It is clear from the ground and the area is well drained and ventilated. H3 treatment is designed to prevent attack by insects, including termites, and decay.

Hazard Class H4 defines the requirements for "severe decay, borers and termites", fence posts, greenhouses, pergolas (in ground and landscaping timbers)". The timber to which H4 is applicable is in contact with the ground or is continually damp so there is a severe decay hazard. The treatment stops attack by insects, including termites, and severe decay.

"Penetration" is defined under the H3/H4 Standards as: "All preservative-treated wood shall show evidence of distribution of the preservative in the penetration zone in accordance with the following requirements: (a) If the species of timber used is of natural durability class 1 or 2, the preservative shall penetrate all the sapwood. Preservative penetration of the heartwood is not required; (b) If the species of timber used is of natural durability class 3 or 4, the preservative shall penetrate all of the sapwood and, in addition one of the following requirements shall apply; (b(i)) Where the lesser cross-sectional dimension is greater than 35 mm, the penetration shall be not less than 8 mm from any surface. Where the lesser cross-sectional dimension is equal or less than 35 mm, the penetration shall be not less than 5 mm from any surface; and (b(ii)) Unpenetrated heartwood shall be permitted, provided that it comprises less than 20% of the cross-section of the piece and does not extend more than halfway through the piece from one surface to the opposite surface and does not exceed half the dimension of the side in the cross-section on which it occurs".

As mentioned above, a carrier must be used in order to facilitate penetration of the preservative into the timber. As shown in the Australian Standards, the carriers presently available can be characterised broadly as "water-borne" or "solvent-borne" systems.

A carrier must be capable of providing sufficient penetration of the preservative into the wood, thereby to provide an effective barrier against infestation. Other considerations in the choice of carrier include the desired rate of penetration, cost, environmental, health and safety considerations. A carrier may provide for a "complete penetration" formulation, or for an "envelope penetration" formulation in which a defined depth of penetration of one or more preservatives into the wood is achieved.

The preservatives commonly used in timber treatment can be characterised according to the carrier vehicle used to carry preservatives into the timber, and by the active ingredients protecting against the various hazards. Light organic solvent-borne preservatives (LOSPs) comprise a light organic solvent, typically white spirits, to carry the preservative into the timber. The solvent is drawn out in the final stages of treatment, with the preservative remaining within the wood. Such preservatives are typically fungicides, having copper, tin, zinc, azoles and pentachlorophenols (PCPs) as major toxicants. Insecticides such synthetic pyrethroids (e.g., permethrin, cypermthrin or bifenthrin) may be incorporated within the preservative composition if an insect hazard is also present.

One principal advantage of LOSP and other hydrocarbon solvent-based treatments is that the treated timber does not swell, making such treatment suitable for "finished" items such as mouldings and joinery. The majority of LOSPs used in wood treatment also contain mixtures of resin/waxes so as to give the surface water repellent properties. However, odour and exposure to VOCs (volatile organic compounds) can present some environmental/occupational health and safety issues. The LOSP procedure does engender one significant advantage in that it does not add moisture back into the timber. Excessive moisture uptake can affect the dimensional stability of timber.

It is an object of the present invention to overcome or ameliorate at least one of the disadvantages of the prior art, or to provide a useful alternative.

The present invention thereby seeks to provide a wood treatment formulation that meets the industry-specific standards of active ingredient retention and penetration. The treated wood should preferably not require re-drying after treatment and have good dimensional stability. The advantages in obtaining an industrially-effective "low odour preservative" formulation may be both economic and environmental.

Low aromatic or dearomatised solvents are proposed herein as an alternative to LOSP/mineral spirits, kerosene, diesel—or indeed any other solvent-based hydrocarbon carrier currently used throughout the wood preservation industry. For example, carriers according to the invention can comprise low odour solvents or mixtures of solvents, which can be considered as dearomatised solvents or low aromatic solvents, that contain wood preservatives for the treatment of wood and wood products.

Low odour solvents have been prescribed in, for instance, International patent publication WO 2000/066668. This document describes a composition comprising: (a) a hydrocarbon component; and (b) an ester component; wherein the composition has: (i) less than 13% vol. of aromatic compounds relative to the total volume of the composition; (ii) a distillation range situated within the range 135-260° C.; and (iii) a Kauri butanol value of 34 or more.

For clarity, it will be appreciated by those of skill in the art that the low odour solvent or solvent mixture need not be free or even substantially free of aromatics; an upper aromatics content of approximately 15% v/v is envisaged. As such—and for the avoidance of doubt, a solvent mixture comprising 85% v/v Exxsol® D40 (discussed below) and 15% v/v kerosene is considered "low odour" for the purposes of the present invention. "Low odour" and "low aromatic" are used synonymously throughout.

A non-limiting example of low aromatic solvents available in industry are those manufactured by ExxonMobil Chemical Company; the Exxsol® D and Isopar® fluid ranges. Such products are purported to give rise to improved health benefits for the workplace by way of a low order of acute toxicity; not classified for skin irritation and does not cause skin sensitisation; lower aromatic leading to increased worker comfort; and non-carcinogenic properties. These solvents also give rise to improved environmental performance such that they do not cause stratospheric ozone depletion. Moreover, Exxsol® D and Isopar® fluids meet certain US FDA Regulations (21 CFR), on an ex-plant basis.

TABLE 1

Comparison of health factors using traditional LOSP carriers versus selected Exxsol ® D and Isopar ® fluids

| Properties | Mineral Spirit | Kerosene | Diesel | Exxsol® D40 | Exxsol® D80 | Isopar® G | Isopar® L | Isopar® M |
|---|---|---|---|---|---|---|---|---|
| Boiling Range | 150-200° C. | 150-290° C., or wider | 180-365° C., or wider | 150-196° C. | 200-250° C. | 153-180° C. | 182-205° C. | 218-257° C. |
| Flash Point | 35-40° C. | 37-65° C. | >55° C. | 40° C. min | 75° C. min | 40° C. min | 62° C. min | 80.5° C. min |
| Composition: | | | | | | | | |
| Aliphatics | ✓ | ✓ | ✓ | ✓ | ✓ | ✓ | ✓ | ✓ |
| Aromatics | ✓ (up to 20 + wt %) | ✓ (up to 20 + wt %) | ✓ (up to 30 + wt %) | ✗ (<1 wt %) | ✗ (<1 wt %) | ✗ (<0.05 wt %) | ✗ (<0.05 wt %) | ✗ (<0.05 wt %) |
| PNA[c] | ✗ | ✗ | ✓ | ✗ | ✗ | ✗ | ✗ | ✗ |
| OEL[a] | 300 mg/m$^3$ (~50 ppm) | 200 mg/m$^3$ (~40 ppm) | 100 mg/m$^3$ (~20 ppm) | 1200 mg/m$^3$ (197 ppm) | 1200 mg/m$^3$ (165 ppm) | 1200 mg/m$^3$ (196 ppm) | 1200 mg/m$^3$ (171 ppm) | 1200 mg/m$^3$ (152 ppm) |
| VHR[b] | ~45 | ~100 | ~150 | 13 | 1.4 | 12 | 4 | 0.6 |
| "Low" Odour | ✗ | ✗ | ✗ | ✓ | ✓ | ✓ | ✓ | ✓ |

[a]Occupational exposure limit
[b]Vapour hazard ratio
[c]Polynuclear aromatic hydrocarbons Exxsol® D and Isopar® fluids are well defined solvents, with narrow boiling ranges that have been subjected to additional distillation and refining (cf. kerosene, etc.). When purified to this extent, they are found to be practically free of aromatics, which in turn brings forth perceptible advantages in that traditional aromatic hydrocarbons are associated with adverse health effects.

As can be seen from Table 1, above, mineral spirits, kerosene and diesel have wide boiling ranges; their composition varies significantly; and certain solvent behaviours can on occasion be difficult to predict. They may contain hazardous constituents such as naphthalene and/or ethyl benzene (naphthalene is classified as "Group 2B" carcinogen, i.e., possibly carcinogenic to Humans, by the International Agency for Research on Cancer, for effects seen at the nasal area of rodents; ethyl benzene carries the same classification given tumour growth in the kidneys of rodents).

TABLE 2

Comparison of potential environmental classification using traditional LOSP carriers versus selected Exxsol ® D and Isopar ® fluids

| Properties | Mineral Spirit | Kerosene | Diesel | Exxsol ® D40 | Exxsol ® D80 | Isopar ® G | Isopar ® L |
|---|---|---|---|---|---|---|---|
| Current EU classification | R51/53 | R51/53 | R51/53 | Not classified | Not classified | R53 | Not classified |
| Predicted GHS classification | Acute II Chronic II | Acute II Chronic II | Acute II Chronic II | Chronic IV | Chronic IV | Acute III Chronic III | Not classified |

51/53: Toxic to aquatic organisms, may cause long term adverse effects in the aquatic environment
R53: May cause long term adverse effects in the aquatic environment
GHS: Globally harmonised system of classification and labelling of chemicals Diesel, on the other hand, contains polynuclear aromatic hydrocarbons (PNAs). Certain PNAs have carcinogenic properties—and indeed, diesel is classified for carcinogenicity in Europe.

By comparison, Exxsol® D and Isopar® fluids have a significantly higher Occupational Exposure Limit. Exxsol® D and Isopar® fluids are free of naphthalene and ethyl benzene. Further, the Vapour Hazard Ratio (VHR) for Exxsol® D & Isopar® fluids are significantly lower than the corresponding measures for mineral spirits, kerosene or diesel, meaning that it is far easier to be "overexposed" to traditional wood preservative carriers. In fact, low aromatic solvents can be so gentle as to allow for their use within personal care products. To this end, the Isopar® fluids are registered with the Personal Care Products Council (formerly, the CTFA).

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

Although the invention will be described with reference to specific examples it will be appreciated by those skilled in the art that the invention may be embodied in many other forms.

SUMMARY OF THE INVENTION

The present invention relates generally to the use of one or more low aromatic, or substantially low aromatic solvents in a carrier for a wood preservative. The one or more low aromatic, or substantially low aromatic solvents can be white spirit, kerosene, a dearomatised solvent, a paraffin solvent, an isoparaffin solvent, a naphthenic solvent, a solvent derived from a source that is naturally low in aromatics or mixtures thereof, or solvents that are equivalent or near equivalent in specification. The carrier may comprise an aromatics content up to about 15% v/v. The wood preservative may comprise tebuconazole, propiconazole and permethrin as biocidally-active agents. The carrier may further comprise one or more co-solvents to solubilise the biocidally-active agents.

The present invention also relates generally to carrier system for use in a wood preservative formulation, said carrier system comprising one or more low aromatic, or substantially low aromatic solvents. The low aromatic solvent can be white spirit, kerosene, a dearomatised solvent, a paraffin solvent, an isoparaffin solvent, a naphthenic solvent, a solvent derived from a source that is naturally low in aromatics or mixtures thereof, or solvents that are equivalent or near equivalent in specification. The carrier system may comprise an aromatics content up to about 15% v/v. The preservative may comprise tebuconazole, propiconazole and permethrin as biocidally-active agents. The carrier system may further comprise one or more co-solvents to solubilise the biocidally-active agents.

The present invention also relates generally to a preservative formulation for use in treating wood or other cellulosic materials, said formulation comprising at least one preservative; and a carrier system comprising one or more low aromatic, or substantially low aromatic solvents. The one or more low aromatic, or substantially low aromatic solvents can be white spirit, kerosene, a dearomatised solvent, a paraffin solvent, an isoparaffin solvent, a naphthenic solvent, a solvent derived from a source that is naturally low in aromatics or mixtures thereof, or solvents that are equivalent or near equivalent in specification. The carrier system can comprise an aromatics content up to about 15% v/v. The preservative may comprise tebuconazole, propiconazole and permethrin as biocidally-active agents. The carrier system may further comprise one or more co-solvents to solubilise the biocidally-active agents.

The present invention also relates generally to a method of treating a substrate of wood or other cellulosic materials which comprises applying to the substrate a preservative formulation comprising: at least one preservative in a carrier system comprising one or more low aromatic, or substantially low aromatic solvents. The one or more low aromatic, or substantially low aromatic solvents can be white spirit, kerosene, a dearomatised solvent, a paraffin solvent, an isoparaffin solvent, a naphthenic solvent, a solvent derived from a source that is naturally low in aromatics or mixtures thereof, or solvents that are equivalent or near equivalent in specification. The carrier system can comprise an aromatics content up to about 15% v/v. The preservative may comprise tebuconazole, propiconazole and permethrin as biocidally-active agents. The carrier system may further comprise one or more co-solvents to solubilise the biocidally-active agents.

The present invention also relates generally to treated wood or engineered wood products, when treated by a method which comprises applying to the substrate a preservative formulation comprising: at least one preservative in a carrier system comprising one or more low aromatic, or substantially low aromatic solvents. The one or more low aromatic, or substantially low aromatic solvents is white spirit, kerosene, a dearomatised solvent, a paraffin solvent, an isoparaffin solvent, a naphthenic solvent, a solvent derived from a source that is naturally low in aromatics or mixtures thereof, or solvents that are equivalent or near equivalent in specification. The carrier system may comprise an aromatics content up to about 15% v/v. The preservative may comprise tebuconazole, propiconazole and permethrin as biocidally-active agents. The carrier system may further comprise one or more co-solvents to solubilise the biocidally-active agents.

The present invention also relates generally to method of preparing a formulation for treating wood, the method comprising the step of admixing a preservative mixture, and a carrier system comprising one or more low aromatic, or substantially low aromatic solvents. The one or more low aromatic, or substantially low aromatic solvents can be white spirit, kerosene, a dearomatised solvent, a paraffin solvent, an isoparaffin solvent, a naphthenic solvent, a solvent derived from a source that is naturally low in aromatics or mixtures thereof, or solvents that are equivalent or near equivalent in specification. The carrier system may comprise an aromatics content up to about 15% v/v. The preservative mixture may comprise tebuconazole, propiconazole and permethrin as biocidally-active agents. The carrier system may further comprise one or more co-solvents to solubilise the biocidally-active agents.

The present invention also relates generally to a formulation comprising: tebuconazole, propiconazole and permethrin diluted in a carrier system comprising one or more solvents such that the aromatic component of the carrier is less than about 15% v/v. The one or more solvents can be white spirit, kerosene, a dearomatised solvent, a paraffin solvent, an isoparaffin solvent, a naphthenic solvent, a solvent derived from a source that is naturally low in aromatics or mixtures thereof, or solvents that are equivalent or near equivalent in specification. The one or more solvents have a flash point equal to or greater than 61° C. The formulation optionally further comprises mouldicides, antifoam agents, water repellent components, fire retardants, colour additives, adhesion promoters, penetration marker compounds or other additives. The formulation optionally further comprises an amount of water, such that the moisture content of timber treated with said formulation remains less than 30% immediately after treatment.

The present invention also relates generally to a method of treating a substrate of *pinus radiata, pinus elliotti* (including its hybrids) or *pinus pinaster* timber which comprises applying to the substrate a preservative formulation comprising: at least one preservative in a carrier system comprising one or more low aromatic, or substantially low aromatic solvents. The method is applied at a rate or uptake sufficient to achieve penetration of the at least one preservative to the core of said substrate. The penetration to the core of the substrate is compliant with AS1604 or NZS3640 series standards. The one or more low aromatic, or substantially low aromatic solvents can be white spirit, kerosene, a dearomatised solvent, a paraffin solvent, an isoparaffin solvent, a naphthenic solvent, a solvent derived from a source that is naturally low in aromatics or mixtures thereof, or solvents that are equivalent or near equivalent in specification; and said carrier system comprises an aromatics content up to about 15% v/v. The preservative formulation comprises tebuconazole, propiconazole and permethrin as biocidally-active agents dissolved in one or more co-solvents.

Thus, according to a first aspect of the present invention there is provided the use of one or more low aromatic, or substantially low aromatic solvents as a carrier for a wood preservative.

In an embodiment, the low aromatic solvent is selected from the group consisting of Exxsol® D and Isopar® fluids. Preferably, the low aromatic solvent is selected from the group consisting of Exxsol® D hexane; Exxsol® D heptane; Exxsol® DSP 80/100; Exxsol® D30; Exxsol® D40; Exxsol® D60; Exxsol® D80; Exxsol® D110; Exxsol® D130; Isopar® C; Isopar® E; Isopar® G; Isopar® H; Isopar® L; Isopar® M.

In an embodiment, the use comprises two low aromatic solvents in a ratio from about 1:99 to about 99:1 w/w. Preferably, the ratio is about 50:50 w/w. in an embodiment, the two low aromatic solvents are Exxsol® D60 and Exxsol® D80. In a preferred embodiment employing one solvent, the low aromatic solvent is preferably Exxsol® D40, Exxsol® D60 or Exxsol® D80.

According to a second aspect of the present invention there is provided a preservative formulation for use in treating wood or other cellulosic formulations, said formulation comprising: at least one preservative; and a carrier comprising one or more low aromatic, or substantially low aromatic solvents.

The low aromatic solvent is selected from the group consisting of Exxsol® D and Isopar® fluids. Preferably, the low aromatic solvent is selected from the group consisting of Exxsol® D hexane; Exxsol® D heptane; Exxsol® DSP 80/100; Exxsol® D30; Exxsol® D40; Exxsol® D60; Exxsol® D80; Exxsol® D110; Exxsol® D130; Isopar® C; Isopar® E; Isopar® G; Isopar® H; Isopar® L; Isopar® M.

In an embodiment, there are two low aromatic solvents in a ratio from about 1:99 to about 99:1 w/w. Preferably, the ratio is about 50:50 w/w. in an embodiment, the two low aromatic solvents are Exxsol® D60 and Exxsol® D80. In another preferred embodiment employing one solvent, the low aromatic solvent is preferably Exxsol® D60 or Exxsol® D80. In another embodiment, the formulation comprises one or more biocidal compounds. In a preferred embodiment, the formulation contains biocides selected from the group consisting of: insecticides, termiticides, fungicides, mouldicides, or the like, and mixtures thereof.

In a preferred embodiment, the fungicidal compound or compounds (in the case of mixtures) is a compound selected from the group consisting of: azoles or triazoles, e.g., azaconazole, tebuconazole, propiconazole, cyproconazole, hexaconazole, triadamefon; isothiazolinones, e.g., 4,5-dichloro-2-n-octyl-4-isothiazolin-3-one (DCOIT); quaternary ammonium compounds, e.g didecyldimethylammonium chloride, didecyldimethylammonium carbonate/bicarbonate, N,N-didecyl-N-methyl-N-(polyoxyethyl)ammonium propionate, benzalkonium chloride; and other fungicides such as penflufen, 3-iodo-2-propynyl-butylcarbamate (IPBC), copper naphthenate, copper oxine, copper octanoate, copper soaps, zinc naphthenate, zinc octanoate, zinc soaps, tributyltin naphthenate, chlorothalonil, pentachlorophenol.

Preferably the insecticide or termiticide is selected from the group consisting of: synthetic pyrethroids (such as allethrin, bifenthrin, cyfluthrin, cypermethrin, cyphenothrin, decamethrin, deltamethrin, permethrin, prallethrin, resmethrin, sumithrin, tetramethrin, tralomethrin, transfluthrin, imiprothrin), or other insecticides such as abamectin, chlorfenapyr, chlorpyifos, thiachloprid, etofenprox, fipronil, imidachloprid acetamiprid, clothianidin, dinotefuran, nitenpyram, thiamethoxam and the like, and mixtures thereof.

Preferably, the triazole compound is tebuconazole (α-[2-(4-chlorophenyl)ethyl]-α-(1,1-dimethylethyl)-1H-1,2,4-triazole-1-ethanol) or hexaconazole (α-butyl-α-(2,4-dichlorophenyl)-1H-1,2,4-triazole-l-ethanol). In a preferred embodiment, the triazole compound is propiconazole (1-[[2-(2,4-dichlorophenyl)-4-propyl-1,3-dioxolan-2-yl]methyl]-1H-1,2,4-triazole) or azaconazole (1-[[2,4-dichlorophenyl)-

1,3-dioxolan-2-yl]methyl]-1H-1,2,4-triazole); or difenoconazole (1-[2-[2-chloro-4-(4-chlorophenoxy)phenyl]-4-methyl-1,3-dioxolan-2-ylmethyl]-1H-1,2,4-triazole).

In a preferred embodiment, the preservative is a triazole compound selected from the group consisting of: azaconazole, bromuconazole, cyproconazole, diclobutrazol, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, penconazole, propiconazole, prothioconazole, quinconazole, simeconazole, tebuconazole, tetraconazole, triadimefon, triadimenol, triticonazole, uniconazole, and uniconazole-P.

Most preferably, the triazole is a mixture of tebuconazole and propiconazole. In a preferred embodiment, the biocidal compound are present in unmodified or modified forms. A modified form preferably comprises a chemical or physical modification providing relatively increased stability against environmental conditions such as heat and/or chemical degradation. A modified form may be a microencapsulated form and/or a micronised form.

In a preferred embodiment, the formulation comprises below about 10% w/w biocide content; preferably below about 5%, and more preferably below about 2%.

The carrier can be any low aromatic solvent eliciting the health and safety benefits alluded to above. In a preferred embodiment, the carrier is Exxsol® D60 or Exxsol® D80. In other embodiments, the carrier may be a combination of one or more Exxsol® D and Isopar® fluids and can even be a combination of low aromatic and traditional LOSP solvents, as long as an appropriate efficacy is maintained within the resultant carrier mixture.

In a preferred embodiment, the preservative penetration within the treated wood is by way of substantially complete penetration. Preferably the substantially complete penetration is in accordance with Hazard Class H3 of the Australian Standard AS 1604-2012 series. In a preferred embodiment, the treated wood is classifiable in the art as "dry after" (moisture content <15% w/w) following treatment with the treatment formulation comprising the low aromatic solvent carrier. In a preferred embodiment, the treated wood does not require a substantial subsequent drying operation. In an embodiment the formulation is applicable to hardwood and/or softwood species.

According to another form of the present invention there is provided a method of treating a substrate of wood or other cellulosic formulation which comprises applying to the substrate a preservative formulation as defined immediately above.

Preferably the step of contacting the wood is performed by means selected from the group consisting of: pressure application, vacuum application, spraying, dipping, rolling, painting, or any combination thereof. However, it will be readily appreciated that the invention is applicable to other types of timber, such as sawn logs and the like.

The method optionally comprises at least one vacuum step, more preferably being between about 0 and −50 kPa. The method optionally further comprises at least one pressure step, preferably being between about 0 and 100 kPa. Preferably each vacuum and/or pressure step is held for between about 0 and 10 minutes.

In a preferred embodiment, the dimensional changes between the wood prior to and post the treatment are no greater than about 2 mm in any or either cross-sectional dimension. In another preferred embodiment a final vacuum step is applied, the final vacuum step taking place when said wood is no longer exposed to the preservative formulation. Preferably the final vacuum step is between about 0 and −95 kPa and is held from about 0 to 60 minutes.

According to another form of the present invention there is provided treated wood, when so-treated by a method defined immediately above.

According to another form of the invention there is provided a method of preparing a formulation for treating wood, the method comprising the step of admixing a preservative mixture defined above, with a low aromatic solvent carrier.

According to another form of the invention there is provided a formulation for treating wood, when prepared by a method as defined above.

According to one preferred form of the invention there is provided the use of one or more low aromatic, or substantially low aromatic solvents in a carrier for a wood preservative.

In an embodiment, the one or more low aromatic, or substantially low aromatic solvents is white spirit, kerosene, a dearomatised solvent, a paraffin solvent, an isoparaffin solvent, a naphthenic solvent, a solvent derived from a source that is naturally low in aromatics or mixtures thereof, or solvents that are equivalent or near equivalent in specification. In another embodiment, the carrier comprises an aromatics content up to about 15% v/v. In another embodiment, the wood preservative comprises tebuconazole, propiconazole and an insecticide as biocidally-active agents. In another preferred embodiment, the insecticide is permethrin. In another preferred embodiment, the carrier further comprises one or more co-solvents to solubilise the biocidally-active agents.

According to another preferred form of the invention there is provided a carrier system for use in a wood preservative formulation, said carrier system comprising one or more low aromatic, or substantially low aromatic solvents. In an embodiment, the low aromatic solvent is white spirit, kerosene, a dearomatised solvent, a paraffin solvent, an isoparaffin solvent, a naphthenic solvent, a solvent derived from a source that is naturally low in aromatics or mixtures thereof, or solvents that are equivalent or near equivalent in specification. In another embodiment, the carrier system comprises an aromatics content up to about 15% v/v. In another embodiment, the preservative comprises tebuconazole, propiconazole and an insecticide as biocidally-active agents. In another preferred embodiment, the insecticide is permethrin. In another preferred embodiment, the carrier system comprises one or more co-solvents to solubilise the biocidally-active agents.

According to another preferred form of the invention there is provided a preservative formulation for use in treating wood or other cellulosic materials, said formulation comprising: at least one preservative; and a carrier system comprising one or more low aromatic, or substantially low aromatic solvents.

In an embodiment, the one or more low aromatic, or substantially low aromatic solvents is white spirit, kerosene, a dearomatised solvent, a paraffin solvent, an isoparaffin solvent, a naphthenic solvent, a solvent derived from a source that is naturally low in aromatics or mixtures thereof, or solvents that are equivalent or near equivalent in specification. In an embodiment, the carrier system comprises an aromatics content up to about 15% v/v. In an embodiment, the preservative comprises tebuconazole, propiconazole and permethrin as biocidally-active agents. In an embodiment, the carrier system further comprises one or more co-solvents to solubilise the biocidally-active agents.

According to another preferred form of the invention there is provided a method of treating a substrate of wood or other cellulosic materials which comprises applying to the substrate a preservative formulation comprising: at least one preservative in a carrier system comprising one or more low aromatic, or substantially low aromatic solvents.

In an embodiment, the one or more low aromatic, or substantially low aromatic solvents is white spirit, kerosene, a dearomatised solvent, a paraffin solvent, an isoparaffin solvent, a naphthenic solvent, a solvent derived from a source that is naturally low in aromatics or mixtures thereof, or solvents that are equivalent or near equivalent in specification. In an embodiment, the carrier system comprises an aromatics content up to about 15% v/v. In an embodiment, the preservative comprises tebuconazole, propiconazole and an insecticide as biocidally-active agents. In another preferred embodiment, the insecticide is permethrin. In another preferred embodiment, the carrier system further comprises one or more co-solvents to solubilise the biocidally-active agents.

According to another preferred form of the invention there is provided treated wood or engineered wood products, when so-treated by a method which comprises applying to the substrate a preservative formulation comprising: at least one preservative in a carrier system comprising one or more low aromatic, or substantially low aromatic solvents.

In an embodiment, the one or more low aromatic, or substantially low aromatic solvents is white spirit, kerosene, a dearomatised solvent, a paraffin solvent, an isoparaffin solvent, a naphthenic solvent, a solvent derived from a source that is naturally low in aromatics or mixtures thereof, or solvents that are equivalent or near equivalent in specification. In an embodiment, the carrier system comprises an aromatics content up to about 15% v/v. In an embodiment, the preservative comprises tebuconazole, propiconazole and an insecticide as biocidally-active agents. In an embodiment, the one or more insecticides comprise permethrin, bifenthrin, cypermethrin, deltamethrin, imidacloprid and thiacloprid.

According to another preferred form of the invention there is provided a method of preparing a formulation for treating wood, said method comprising the step of admixing a preservative mixture, and a carrier system comprising one or more low aromatic, or substantially low aromatic solvents. In an embodiment, the one or more low aromatic, or substantially low aromatic solvents is white spirit, kerosene, a dearomatised solvent, a paraffin solvent, an isoparaffin solvent, a naphthenic solvent, a solvent derived from a source that is naturally low in aromatics or mixtures thereof, or solvents that are equivalent or near equivalent in specification. In an embodiment, the carrier system comprises an aromatics content up to about 15% v/v. In an embodiment, the preservative mixture comprises tebuconazole, propiconazole and an insecticide as biocidally-active agents. In another preferred embodiment, the insecticide is permethrin. In another preferred embodiment, the carrier system further comprises one or more co-solvents to solubilise the biocidally-active agents.

According to another preferred form of the invention there is provided a formulation comprising: tebuconazole, propiconazole and an insecticide diluted in a carrier system comprising one or more solvents such that the aromatic component of the carrier is less than about 15% v/v.

In a preferred embodiment, the insecticide is permethrin. In another preferred embodiment, the one or more solvents is white spirit, kerosene, a dearomatised solvent, a paraffin solvent, an isoparaffin solvent, a naphthenic solvent, a solvent derived from a source that is naturally low in aromatics or mixtures thereof, or solvents that are equivalent or near equivalent in specification. In another preferred embodiment, the formulation has a flash point equal to or greater than 61° C. In another preferred embodiment, the formulation optionally further comprises mouldicides, antifoam agents, water repellent components, fire retardants, colour additives, adhesion promoters, penetration marker compounds or other additives. In another preferred embodiment, the formulation optionally further comprises an amount of water, such that the moisture content of timber treated with said formulation remains less than 30% immediately after treatment.

According to another preferred form of the invention there is provided a method of treating a substrate of *pinus radiata, pinus elliotti* (including its hybrids), *pinus* caribaea (including its hybrids) or *pinus pinaster* timber which comprises applying to the substrate a preservative formulation comprising: at least one preservative in a carrier system comprising one or more low aromatic, or substantially low aromatic solvents.

In an embodiment, the formulation has a flash point of greater than about 61° C. In an embodiment, the formulation is applied at a rate or uptake sufficient to achieve penetration of the at least one preservative to the core of said substrate. In an embodiment, the penetration to the core of said substrate is compliant with AS1604 or NZS3640 series standards. In an embodiment, the one or more low aromatic, or substantially low aromatic solvents is white spirit, kerosene, a dearomatised solvent, a paraffin solvent, an isoparaffin solvent, a naphthenic solvent, a solvent derived from a source that is naturally low in aromatics or mixtures thereof, or solvents that are equivalent or near equivalent in specification; and said carrier system comprises an aromatics content up to about 15% v/v. In an embodiment, the preservative formulation comprises tebuconazole, propiconazole and permethrin as biocidally-active agents dissolved in one or more co-solvents.

The compositions according to the invention may be used to treat substrates such as wood or other cellulosic formulations (such as cotton, hessian, rope and cordage). For convenience, the invention is described with reference to the treatment of wood, but it will be appreciated that the other formulations may be treated analogously.

The inventive compositions may contain more than one triazole compound for example, they may contain tebuconazole and propiconazole, or a mixture of tebuconazole, propiconazole and azaconazole. Compositions may contain more than one triazole compound. For example, they may contain tebuconazole and propiconazole, or a mixture of tebuconazole, propiconazole and azaconazole.

The compositions of the present invention may advantageously contain a biocidally-active quaternary ammonium compound or tertiary amine salt.

The compositions in accordance with the invention comprise one or more low aromatic solvents as the carrier (or even as a constituent of the carrier). Formulations can be prepared as concentrates intended to be diluted at the treatment facility, or the formulations can be prepared in the form of "ready-to-use" treatment solutions. Optionally, separate solutions of preservatives and triazole compound can be provided, e.g., in the form of two concentrates intended to be mixed before or after dilution.

Compositions in accordance with the invention can optionally contain other additives conventionally employed in timber preservation such as water repellents, mouldicides, colour additives, adhesion promoters, corrosion inhibitors or penetration marker compounds. The latter refer to compounds that are included in the formulation to demonstrate the penetration of the active ingredients, in cases where there are no known spot tests (AS1605.2:2006; AWPA A3-08) for the active ingredients in question. Penetration markers used are commonly divalent metals, complexed with a suitable ligand to afford the appropriate solubility.

The compositions of the invention may contain other organic compounds including fungicides, mouldicides, termiticides, insecticides and bacteriocides. Such organic compounds include carboxylic acids such as naphthenic acids and branched aliphatic acids and their metal salts such as copper and zinc naphthenate, phenols and substituted phenols such as orthophenyl phenol and its alkali metal or ammonia salts; polyhalogenated phenols such as pentachlorophenol or tribromophenol and their alkali metal or ammonia salts; quaternary ammonium salts and tertiary amine salts such as didecyl dimethyl ammonium chloride, octyl decyl dimethyl ammonium chloride, dodecyl dimethyl benzyl ammonium chloride, dodecyl benzyl trimethyl ammonium chloride, dodecyl dimethyl amine acetate, dodecyl dimethyl amine lactate, dodecyl dimethyl amine salicylate, didodecyl methyl amine chloride; isothiazolone derivatives such as 4,5-dichloro-2-(n-octyl)-4-isothiazolin-3-one or 2-methyl-4-isothiazolin-3-one, 2n-octyl-4-isothiazolin-3-one and mixtures of those and other related compounds; sulfamide derivatives such as N,N-dimethyl-N-phenyl-(N-fluorodichloro-methylthio)-sulfonamide, N,N-dimethyl-N-tolyl-N-(dichlorofluoro-methylthio)-sulfamide; azoles such as imidazole; MBT (methylene-bis thiocyanate); IPBC (3-iodo-2-propanyl-butyl-carbamate); carbendazim and chlorothalonil; N-nitrosophenylhydroxylamine and N-nitroso cyclohexyl hydroxylamine, either as their metal salts or as metal chelates; pyrethroid type insecticides selected from the group consisting of cyano-(4-fluoro-3-phenoxy-phenyl)-methyl-3-(2,2-dichioroethenyl)-2,2-dimethyl cyclopropanecarboxylate, (3-phenoxyphenyl)methyl-3-(2,2-dichloro-ethyenyl)-2,2-dimethyl-cyclopropanecarboxylate, cyano-(3-phenoxy-phenyl)-methyl-2-(4-chlorophenyl)-3-methylbutyrate, and mixtures thereof; organophosphorous, carbamate and organochlorine insecticides such as lindane.

Various "low odour" products containing tebuconazole, propiconazole and permethrin as ingredients could contain aromatic concentrations as summarised below.

According to a further form of the present invention there is provided a method of treating timber or another cellulosic substrate of the type hereinbefore described, which comprises applying to the substrate a composition as defined above.

TABLE 3

Exemplary "low odour" tebuconazole, propiconazole and permethrin formulations

| Product[a,b] | Aromatic content |
|---|---|
| "Low odour" wood preservative formulation prepared from Vacsol Azure Wood Preservative Concentrate (VAWPC) diluted with D80 | 0.82% v/v |
| "Low odour" wood preservative formulation in D80 from VAWPC, with a green colourant added at a rate in the range 0.01 to 0.1% v/v | 0.98% v/v |
| "Low odour" wood preservative formulation in D80 from VAWPC, with green colour (as above) and metal tracer added at the appropriate addition rate. | 1.30% v/v |

[a]Vacsol Azure Concentrate Wood Preservative is a proprietary one-pack product containing the active ingredients tebuconazole, propiconazole, permethrin and various inert ingredients including a proprietary water repellent system.
[b]D80 refers to a dearomatised solvent with <0.5% w/w aromatics, boiling point range of approximately 200-250° C., flash point of 80° C.

The skilled person will be well acquainted with the various methods of treating the substrates with wood preservative solutions. For example, the compositions according to the invention may be applied to wood by dipping, spraying, deluging, brushing, vacuum impregnation, pressure impregnation, combinations thereof and/or any other applicable method. Other types of substrate may be treated by analogous methods.

Salient features of the formulations presented in Table 3 include: (a) that the "low odour" solvents may be derived by any known means, including hydrogenation of paraffinic, naphthenic and aromatic mixtures (dearomatisation, e.g., Exxsol® D80), fractionation, liquid-liquid extraction, selective absorption (e.g., with zeolites) or prepared from gas to liquid catalysis (as in the case of isoparaffins); (b) that different boiling point ranges of dearomatised/low aromatic solvents (e.g., D80 and D130) are used; (c) solvents that by nature of the crude oil they are derived from naturally contain low levels of aromatics, e.g., Enersol K; (d) include the substitution of dearomatised/low aromatic solvents by water (perhaps 10-30% v/v) within the formulation, such that the treated articles are still considered as "dry after" (moisture content<fibre saturation point ~30%) and do not require re-drying; (e) the formulation may optionally include other solvents (generally described as "co-solvents"), to solubilise the preservative active ingredients or aid in formulating other additives; typical examples of co-solvents include aromatics, alcohols, glycols, glycol ethers, carbonates, pyrrolidones, esters, ethers, amines, ketones, amides, sulfoxides, lactones, although in practice, some of these co-solvents may not be suitable for low odour products; (f) the dearomatised/low aromatic solvents can be flammable or combustible; (g) the low aromatic solvents may come from any one of numerous producers and suppliers; some of which are given in the Table 4, below.

TABLE 4

Some commercially-available sources of "low odour" solvents
Product name/tradename[a]

| | | | |
|---|---|---|---|
| Exxsol ® Hexane | Isopar ® M | Ketrul 211 | Enersol K |
| Exxsol ® Heptane | ISANE IP 185 | Ketrul D85 | Recosol 78 |
| Exxsol ® DSP 80/100 | ISANE IP 175 | Ketrul D80 | Shellsol TD |
| Exxsol ® D30 | ISANE IP 165 | Ketrul D75 | Shellsol T |
| Exxsol ® D40 | ISANE IP 155 | Ketrul D70 | Shellsol TK |
| Exxsol ® D60 | ISANE IP 130 | Ketrul HT | Shellsol TM |
| Exxsol ® D80 | Hydroseal G 400H | Kerdane | Shellsol D40 |
| Exxsol ® D110 | Hydroseal G 3H | Spirdane D66 | Shellsol D60 |
| Exxsol ® D130 | Hydroseal G 250H | Spirdane K2 | Shellsol D70 |
| Isopar ® C | Hydroseal G 240H | Spirdane D60L | Shellsol D90 |
| Isopar ® E | Hydroseal G 232H | Spirdane D60 | Shellsol D100 |

TABLE 4-continued

Some commercially-available sources of "low odour" solvents
Product name/tradename[a]

| Isopar® G | Ketrul D100 | Spirdane D40K | Cypar 7 |
| Isopar® H | Ketrul 220 | Spirdane D40 | Cypar 9 |
| Isopar® L | Ketrul 212 | Enersol H | YK-D80 |

The preservative compositions according to the present invention are primarily the azole fungicides tebuconazole and propiconazole, with permethrin included as an insecticide. The insecticide could be substituted for other suitable insecticides.

Another alternative to the azoles tebuconazole and propiconazole would be copper naphthenate, although the latter can be problematic when the timber is to be painted in service with light coloured paints.

It may not be essential to use a co-solvent if the product is supplied as a "ready-to-use" solution without water repellent. However, in other embodiments, the use of a co-solvent can be advantageous.

For instance, another aspect of the present invention relates to a formulation comprising: tebuconazole, propiconazole and permethrin dissolved in a suitable co-solvent, diluted with a low odour solvent containing <15% aromatic components and an amount of water, such that the moisture content of timber treated with said formulation remains less than 30% immediately after treatment. In a preferred embodiment, such a formulation optionally comprises surfactants/emulsifiers, other co-solvents, mouldicides, anti-foam agents, water repellent components, colour additives, adhesion promoters, penetration marker compounds or other additives. In an especially preferred embodiment, the low odour solvent is Exxsol® 60 or Exxsol® D80.

The application process by which the inventive carrier and preservative mixture can be applied to the timber is any suitable treatment method for instance, spraying, dipping, deluging, rolling and pressure/vacuum treatment.

In a preferred embodiment, the method of application is vacuum-pressure treatment in an autoclave/treatment cylinder. For the avoidance of doubt, any application process that gives penetration and retention compliance with AS1604, NZS 3640, or other equivalent national standards is applicable to the present invention.

In other especially preferred embodiments, the carrier formulation, incorporating the preservative/s may be applied at elevated temperature.

Another salient feature of the present invention is the uptake of preservative formulation (preservative plus carrier) that can be achieved in practice; uptakes will be somewhat low, generally less than 50 L/m$^3$.

A range of other actives are theoretically possible, for instance: a) A formulation comprising one of more fungicides selected from azaconazole, tebuconazole, propiconazole, cyproconazole, hexaconazole, triadamefon, 4,5-dichloro-2-n-octyl-4-isothiazolin-3-one (DCOIT), didecyldimethylammonium chloride, didecyldimethylammonium carbonate/bicarbonate, N,N-didecyl-N-methyl-N-(polyoxyethyl)ammonium propionate, benzalkonium chloride, penflufen, 3-iodo-2-propynyl-butylcarbamate (IPBC), copper naphthenate, copper oxine, copper octanoate, copper soaps, zinc naphthenate, zinc octanoate, zinc soaps, tributyltin naphthenate, chlorothalonil, pentachlorophenol and an insecticide, formulated in such as way as to enable dilution with a low odour solvent containing <15% aromatic components.

b) A formulation comprising tebuconazole, propiconazole and an insecticide dissolved or suspended [in the case of finely ground (micronized) or precipitated active ingredients] in a suitable co-solvent, diluted with a low odour solvent containing <15% aromatic components. The formulation may optionally contain mouldicides, anti-foam agents, water repellent components, colour additives, adhesion promoters, penetration marker compounds or other additives.

c) A formulation comprising tebuconazole, propiconazole and an insecticide dissolved in a suitable co-solvent, diluted with a low odour solvent, where the low odour solvent is D40, D60 or D80. The formulation may optionally contain mouldicides, anti-foam agents, water repellent components, colour additives, adhesion promoters, penetration marker compounds or other additives.

d) A formulation comprising tebuconazole, propiconazole and permethrin dissolved in a suitable co-solvent, diluted with a low odour solvent containing <15% aromatic components. The formulation may optionally contain mouldicides, anti-foam agents, water repellent components, colour additives, adhesion promoters, penetration marker compounds or other additives.

e) A formulation comprising tebuconazole, propiconazole and imidacloprid dissolved in a suitable co-solvent, diluted with a low odour solvent containing <15% aromatic components. The formulation may optionally contain mouldicides, anti-foam agents, water repellent components, colour additives, adhesion promoters, penetration marker compounds or other additives.

f) A formulation comprising tebuconazole, propiconazole and permethrin dissolved in a suitable co-solvent, diluted with a low odour solvent containing <15% aromatic components and an amount of water, such that the moisture content of the timber treated with such a formulation remains less than 30% immediately after treatment. The formulation may optionally contain surfactants/emulsifiers, extra co-solvents, mouldicides, anti-foam agents, water repellent components, colour additives, adhesion promoters, penetration marker compounds or other additives.

g) A formulation comprising tebuconazole, propiconazole and permethrin dissolved in a suitable co-solvent, diluted with a low odour solvent containing <15% aromatic components, with a flash point equal to or greater than 61° C. The formulation may optionally contain mouldicides, anti-foam agents, water repellent components, colour additives, adhesion promoters, penetration marker compounds or other additives.

h) A formulation comprising tebuconazole, propiconazole and permethrin dissolved in a low odour solvent containing <15% aromatic components. The formulation may optionally contain mouldicides, anti-foam agents, water repellent components, colour additives, adhesion promoters, penetration marker compounds or other additives.

i) A formulation comprising tebuconazole, propiconazole and permethrin dissolved in a low odour solvent containing <15% aromatic components and an amount of water, such that the moisture content of the timber treated with such a formulation remains less than 30% immediately after treatment. The formulation may optionally contain surfactants/emulsifiers, extra co-solvents, mouldicides, anti-foam agents, water repellent components, colour additives, adhesion promoters, penetration marker compounds or other additives.

j) A formulation comprising copper naphthenate and an insecticide dissolved in a low odour solvent containing <15% aromatic components. The formulation may optionally contain mouldicides, anti-foam agents, water repellent components, colour additives, adhesion promoters, penetration marker compounds or other additives.

k) A formulation comprising copper naphthenate and permethrin dissolved in a low odour solvent containing <15% aromatic components. The formulation may optionally contain mouldicides, anti-foam agents, water repellent components, colour additives, adhesion promoters, penetration marker compounds or other additives.

The treated timber can include engineered wood products (EWPs), along with softwoods including (but not limited to), *radiata* pine (*P. radiata*), slash pine (*P. elliottii*), Caribbean pine (*P. caribaea*), the hybrid, maritime pine (*P. pinaster*), Southern yellow pine (including sub-species); and other Asian *pinus* species. The invention is also applicable to the treatment of hardwoods and exotic species.

BRIEF DESCRIPTION OF THE FIGURES

A preferred embodiment of the invention will now be described with reference to the accompanying Figures, in which:

FIG. 4 relates to Example 3.

FIG. 5 also relates to Example 3.

The following Examples are intended to be illustrative of the present invention; they are not to be considered limiting. Indeed, the person skilled in the art will readily appreciate that numerous modifications are possible without departing from the spirit and scope of the present invention.

EXAMPLES

Example 1

An example of a wood preservative formulation containing a low odour solvent is given below in Table 5, below.

TABLE 5

| Exemplary formulation | | |
| --- | --- | --- |
| Raw Material | Function | Concentration (g/L) |
| Vacsol ® Azure Concentrate Wood Preservative[a] | Source of active ingredients, tebuconazole, propiconazole, permethrin and water repellent | 81.8 |
| Green Solvent Pigment Pack | Colour additive | 8 |
| Exxsol ® D80 | Carrier | Balance |

[a]Vacsol Azure Concentrate Wood Preservative is a one-pack product containing the active ingredients tebuconazole, propiconazole, permethrin and various inert ingredients including a proprietary water repellent system.

The formulation was shown to be adequately stable and suitable for use as a solvent-based preservative to treat timber for use in outdoor, above-ground end uses. The low odour wood preservative was used to treat softwood timbers.

Example 2

*Radiata* pine samples (90×35 mm in cross-section, 220 mm long and end-sealed with two-part epoxy resin) were treated with the low odour wood preservative described in Example 1 were wrapped in plastic bags immediately after treatment and stored at ambient temperature.

At the same time, matched samples were treated with a conventional solvent-based preservative, Vacsol® Azure Green C, which uses an aromatic-containing solvent. These samples were also wrapped in plastic bags immediately after treatment and stored under the same conditions as those treated with the low odour wood preservative.

In the case of the samples treated with the formulation described in Example 1, the mean uptake for eight replicates was 50.2 L/m$^3$, which was similar to that for the samples treated with Vacsol® Azure Green C (mean uptake for eight matched replicates was 52.0 L/m$^3$).

Figure 1:
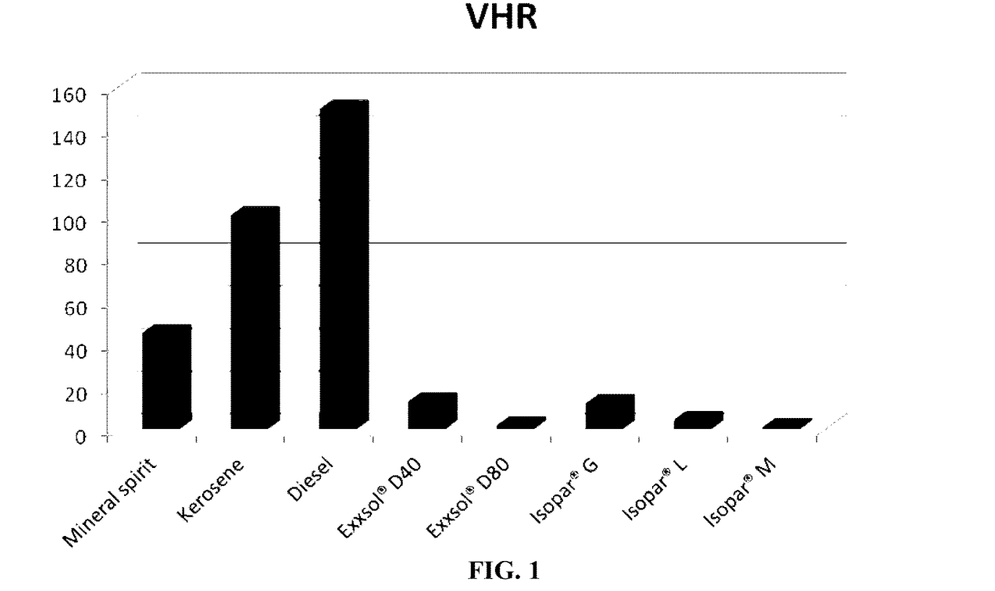
FIG. 1 is graph showing comparative VHR values for the presently-used mineral spirits, kerosene and diesel LOSP carriers versus selected Exxsol® D and Isopar® fluids. VHR reflects the ability of a solvent to evaporate to its OEL. The results indicate a larger margin of safety when using Exxsol® D and Isopar®-type fluids.
Figure 2:
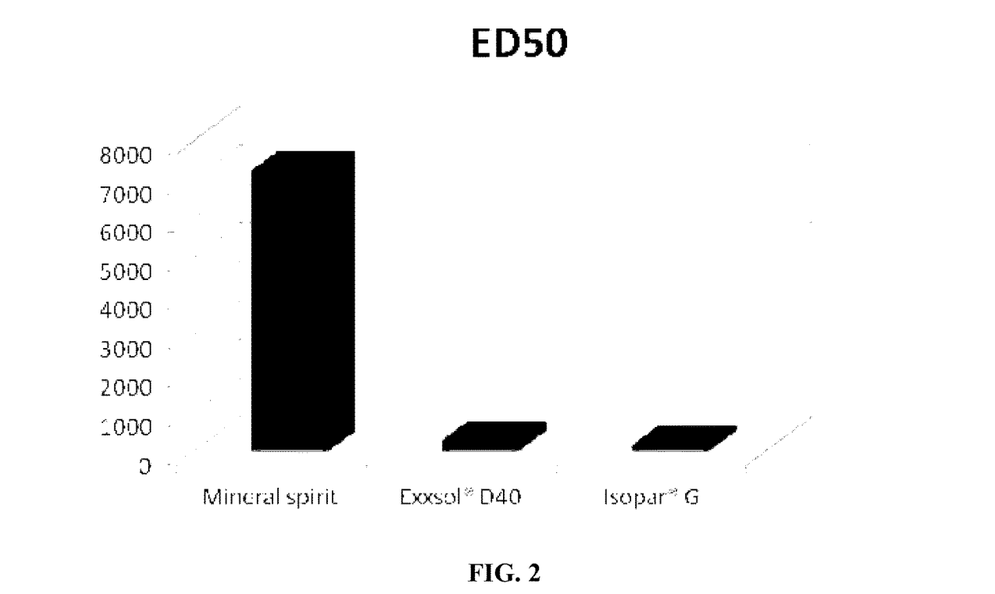
FIG. 2 is a graph showing comparison of odour between mineral spirits and selected Exxsol® D and Isopar® fluids. ED50 is a measure of odour threshold and indicates the dilution factor at which half a test population can no longer detect odour. Higher ED50 values are indicative of a stronger, more penetrating odour. The data show that mineral spirits containing a significant aromatic content has a greater than 30-fold higher ED50 than either Exxsol® D40 or Isopar® G fluids.
Figure 3:
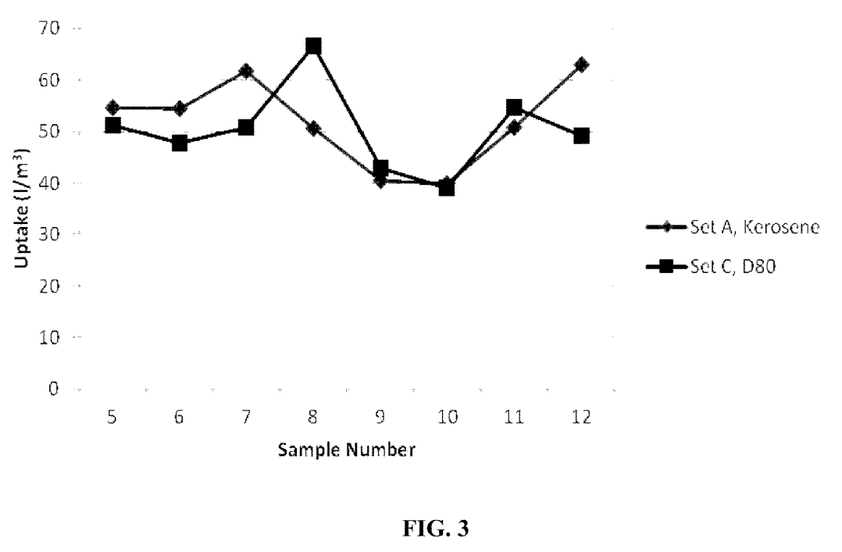
FIG. 3 is relates to Example 2. Individual sample uptakes for *radiata* pine specimens treated with (a) an azole-containing wood preservative formulation utilising D80 as the carrier (red) and (b) a similar preservative where a conventional kerosene solvent was used as the carrier (blue).

The individual specimen uptakes for the two sets of samples are shown in FIG. 3 of the accompanying drawings;

individual sample uptakes for *radiata* pine specimens treated with (a) an azole-containing wood preservative formulation utilising D80 as the carrier (red) and (b) a similar preservative where a conventional kerosene solvent was used as the carrier (blue).

After storage for 4 to 8 weeks, the two sets of samples were periodically unwrapped and shown to various interested persons in a blind test, where the identity of the preservative used to treat the specimens was unknown to the person inspecting the samples.

In each case, the person inspecting the samples commented that those treated with the wood preservative formulation described in Example 1, containing a low aromatic solvent, smelled less noticeably than those treated with the conventional preservative, Vacsol® Azure Green C.

Example 3

It was surprisingly found that the low odour solvent penetrated timber more readily than conventional solvents. It has been postulated previously that solvents with low aromatic content do not penetrate timbers as readily as conventional solvents that contain approximately 15-20% aromatics, particularly in the case of timbers than have naturally high levels of resin.

In this example, end-matched sets (70×35 mm cross-section) of end-sealed slash pine samples were treated with identical preservatives containing a metal naphthenate tracer, formulated in two different solvents. The mean uptake for the set treated with the conventional solvent (kerosene) was 49.6 L/m$^3$, whereas the matching set treated with the low odour solvent (Exxsol® D60, boiling point range 185-199° C., typical aromatic content <0.5% w/w) had a mean uptake of 45.0 L/m$^3$.

Comparing individual specimens, the uptakes were higher for the conventional kerosene solvent preservative, in seven out of ten replicates. Therefore, it was surprising that the metal penetration in the set treated with the low odour solvent was equal to or better in nine of the ten replicates.

Figure 4A:
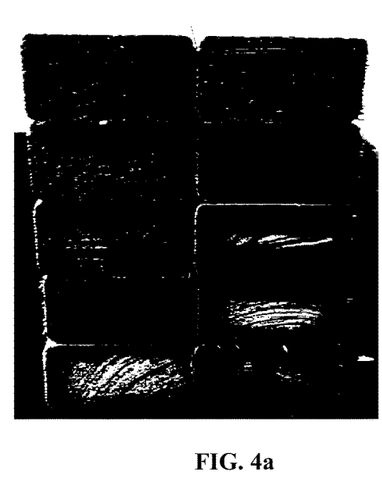
FIG. 4*a* shows samples treated with wood preservative containing a copper naphthenate penetration marker, formulated in low aromatic solvent (D60); the photograph shows the results of penetration assessment, after spraying freshly cut ends with PAN indicator (AWPA A3-08, Method 14).
Figure 4B:
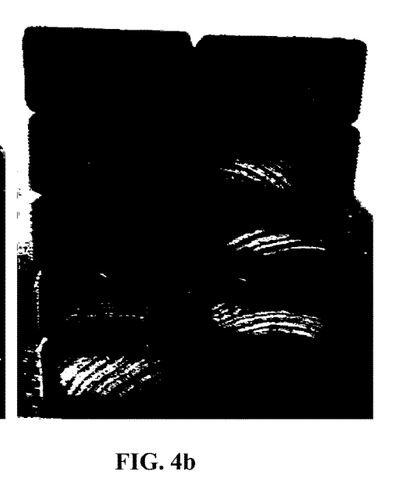
FIG. 4*b* shows samples treated with the same wood preservative formulated in kerosene; the photographs show the results of penetration assessment, after spraying freshly cut ends with PAN indicator (AWPA A3-08, Method 14).

In relation to the accompanying drawings, FIG. 4a shows samples treated with wood preservative formulated in low aromatic solvent (D60); the photograph shows the results of penetration assessment, after spraying freshly cut ends with PAN indicator (AWPA A3-08, Method 14); and FIG. 4b shows samples treated with wood preservative formulated in kerosene; the photographs show the results of penetration assessment, after spraying freshly cut ends with PAN indicator (AWPA A3-08, Method 14).

Figure 5A:
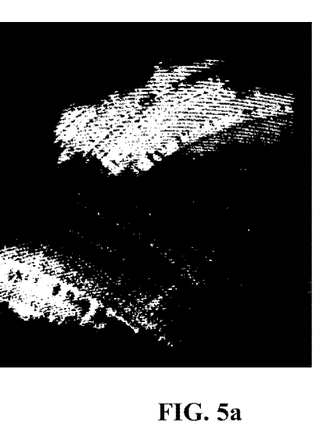
FIG. 5*a* shows samples treated with a wood preservative containing tebuconazole, propiconazole, permethrin and zinc naphthenate as a penetration marker, formulated in kerosene; the photograph shows the results of penetration assessment, after spraying freshly cut ends with PAN indicator (AWPA A3-08, Method 14).
Figure 5B:
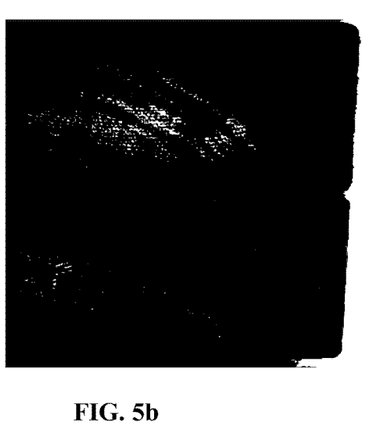
FIG. 5*b* shows samples treated with wood preservative formulated in low aromatic solvent, D80; the photograph shows the results of penetration assessment, after spraying freshly cut ends with PAN indicator (AWPA A3-08, Method 14).

A similar observation has also been made in the treatment of *radiata* pine samples, with an azole containing product where the carrier was either a conventional kerosene with ~20% aromatics (FIG. 5a) or a dearomatised solvent D80 (FIG. 5b). The boiling point range for the D80 solvent (204-246° C.) matched that for the conventional kerosene very closely. The aromatic content in D80 is typically 0.4% w/w.

In both cases the product contained copper naphthenate as a penetration marker. The uptakes in each case were effectively identical.

Having regard to the accompanying drawings, FIG. 5a shows samples treated with wood preservative formulated in kerosene; the photograph shows the results of penetration assessment, after spraying freshly cut ends with PAN indicator (AWPA A3-08, Method 14); and FIG. 5b shows samples treated with wood preservative formulated in low aromatic solvent, D80; the photograph shows the results of penetration assessment, after spraying freshly cut ends with PAN indicator (AWPA A3-08, Method 14).

Example 4

A soil block test was undertaken to compare the antifungal activity of the azoles (tebuconazole and propiconazole) when applied from different solvents, i.e., aromatic-containing solvents, and dearomatised/low aromatic solvents. The results suggest that the azoles applied to wood specimens in a low odour carrier are at least as efficacious as those applied from conventional hydrocarbon solvents containing an appreciable portion of aromatic compounds.

Example 5

The performance of a given preservative is dependent upon a number of factors. For timber that is to be exposed outdoors, one of the most critical factors is the permanence of the fungicidal active ingredients in the wood substrate. In general terms, the more permanent the active ingredients, the better the preservative performance. The azoles tebuconazole and propiconazole are commonly used fungicides in wood preservatives. A comparison of their permanence in timber as a function of different solvent carriers was carried out.

Matched specimens of *radiata* pine sapwood measuring 50×20×20 mm were treated with a series of solvent-based formulations as summarised in Table 6, below. The same process was used to treat the specimens in each case and the uptakes were similar, resulting in similar azole retentions in the treated specimens.

TABLE 6

Summary of preservative/carriers used in leaching study

| Actives[a] | Solvent | Aromatic Content of Solvent (%) |
|---|---|---|
| Tebuconazole, propiconazole, permethrin | White spirit | 20 |
| Tebuconazole, propiconazole, permethrin | Kerosene | 18 |
| Tebuconazole, propiconazole, permethrin | Exxsol ® D60 | <0.5 |
| Tebuconazole, propiconazole, permethrin | Exxsol ® D80 | <0.5 |
| Tebuconazole, propiconazole, permethrin | Exxsol ® D130 | <0.5 |

[a]The inert ingredients in each formulation were identical

After treatment the specimens were placed in polyethylene bags to allow the solvent to evaporate slowly. Once the majority of the solvent had evaporated, the specimens were aired in the open for a further two weeks. The specimens were then subjected to an accelerated leaching study, whereby the specimens were leached in a shaking water bath at 35° C. for seven days, with regular changes of water. The leachate water was retained and analysed for the azoles tebuconazole and propiconazole by HPLC.

From the results of the azole analysis, the Leachability Index (LI) was calculated for each solvent. The LI for each solvent carrier is defined as the percentage of azoles leaching from the timber specimens, relative to that leached from the specimens treated with the white spirit formulation.

If LI is greater than 100, it implies that more azoles were leached from the timber specimens than occurred for white spirit, while if LI is less than 100, it implies that less azoles were leached. The smaller the LI, the more desirable the result, i.e., less azoles leached from the timber. In the experiment described here, unexpectedly the D80-treated samples gave reduced azole leaching.

Figure 6:
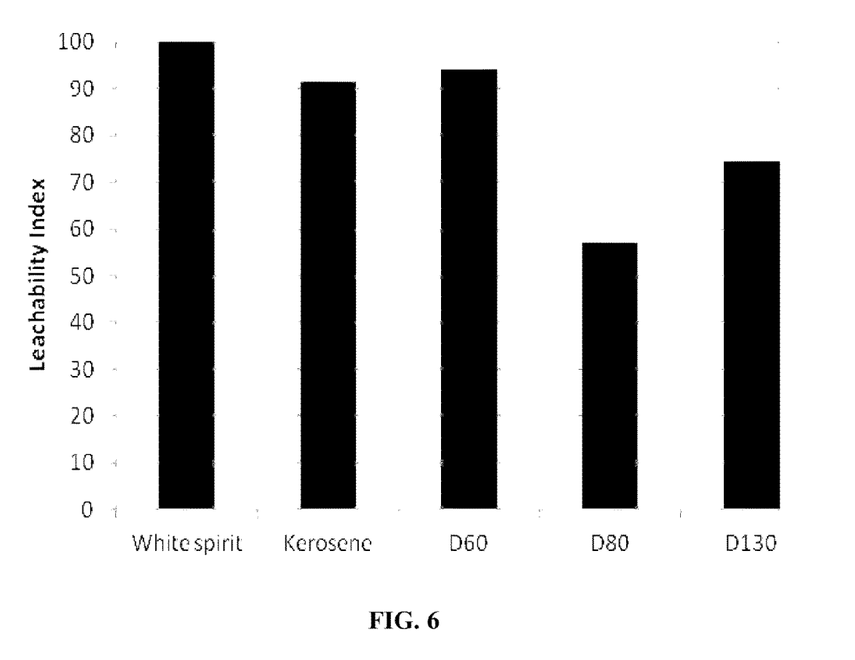
FIG. 6 relates to Example 5. It depicts results from accelerated leaching study comparing the leaching of the azoles, tebuconazole and propiconazole, from *radiata* pine as a function of different solvent carriers. Leachability index=100*(quantity azoles leached from candidate carrier)/(quantity azoles leached from white spirit treatment).

The results are shown in FIG. 6 of the accompanying drawings. The results show the significant and unexpected results for the dearomatised solvent carriers with D80 giving a particularly surprising result.

Example 6

Matched specimens of *radiata* pine framing timber, 90×35 mm in cross-section, were spray-treated with various permethrin-containing formulations (see, Table 7, below), with the objective to meet the penetration requirements of AS1604.1, Table H2.1.

In the case of permethrin, the penetration zone is 5 mm and the minimum active retention in the penetration zone is 0.02% m/m.

It was found that the required depth of penetration could be achieved with formulations containing the low aromatic solvents Exxsol® D110 and Isopar® M, at lower uptake than with Tanalith® T, a product that contains a combination of a drying oil and kerosene as carrier. Exxsol® D110 is a dearomatised solvent (typical boiling point range 249-267° C.) with a typical aromatic content of 0.4% w/w. Isopar® M is an isoparaffin (typical boiling point range 225-254° C.) with a typical aromatic content of 0.01% w/w. The odour of the timber framing treated with D110 or Isopar® M formulations was considerably reduced over that treated with Tanalith® T.

TABLE 7

Summary of results from spray-treatment of framing timbers

| Product/Formulation[a] | Mean Uptake (L/m³) | Penetration[b] |
|---|---|---|
| Tanalith® T | 11.2 | 5 mm penetration achieved |
| Permethrin, blue pigment, zinc octanoate, Exxsol® D110 | 8.1 | 5 mm penetration achieved, depth of penetration uniform |
| Permethrin, blue pigment, zinc octanoate, Exxsol® D110 | 5.9 | 5 mm penetration achieved, less consistently than at higher uptake. Presence of permethrin in the inner 3-5 mm zone confirmed by chemical analysis |
| Permethrin, blue pigment, zinc octanoate, Isopar® M | 10.1 | Penetration somewhat variable. Depth of penetration >5 mm in localised sections |

[a]Formulations contained zinc octanoate as a marker for determination of penetration.
[b]Penetration determined by spraying freshly cut ends with PAN indicator (AWPA A3-08; Method 14).

Example 7

Table 8 shows the results from a laboratory bioassay carried out in accordance with recognised methods (see, Protocols for the Assessment of Wood Preservatives, Australasian Wood Preservation Committee, March 2007 Revision, Ensis, Clayton).

In this test, *radiata* pine sapwood (20×20×10 mm) specimens were treated with a preservative formulation containing tebuconazole, propiconazole and permethrin, formulated in a low aromatic solvent carrier (D80). Three sets of specimens were treated to three different azole retentions, i.e., 0.015, 0.030 and 0.060% m/m total azole (tebuconazole plus propiconazole, with the tebuconazole/propiconazole ratio ~1:1). A further group of specimens were treated with the solvent only, as a control.

After drying, the specimens were saturated with water and leached in a shaking water bath at 35° C. for seven days, with daily changes of water. After leaching, the specimens were vacuum oven dried, before being sterilised in readiness for the fungal bioassay. The specimens were then placed in the soil jars, which had previously been inoculated with the chosen decay fungus, and the jars were incubated under conditions ideal for decay for a period of approximately 12 weeks. After incubation the specimens were cleaned, weighed and their mass loss determined. Mass loss, expressed as a percentage, was used to determine the effectiveness of the preservative treatment. Decay is deemed to have been prevented if the mass loss is less than 3%.

TABLE 8

Summary of results of laboratory decay test. Mass loss (%) in radiata pine sapwood specimens, after exposure to assorted decay fungi.

| Treatment | Azole retention (% m/m) | Mean mass loss (%) | | | | |
|---|---|---|---|---|---|---|
| | | C. olivacea | F. lilacinogilva | G. abietinum | A. xantha | P. tephropora |
| Water | 0 | 59.9 | 62.4 | 38.1 | 55.9 | 42.5 |
| D80 | 0 | 50.5 | 56.8 | 38.4 | 35.4 | 43.3 |
| Tebuconazole, propiconazole, permethrin in a D80 carrier | 0.015 | 0.5 | 26.9 | 0.7 | 7.4 | 0.2 |
| Tebuconazole, propiconazole, permethrin in a D80 carrier | 0.030 | −0.2 | 12.1 | −0.4 | −0.3 | −0.6 |
| Tebuconazole, propiconazole, permethrin in a D80 carrier | 0.060 | −0.1 | 0.5 | −0.9 | −0.2 | −0.4 |

In Table 8, the mass loss for the water- and solvent-treated controls are shown. In each case the mass loss was in excess of 35%, illustrating the viability of the organisms and their capability to decay the *radiata* pine sapwood. The lowest azole retention tested (0.015% m/m) was able to prevent decay of the treated specimens by three of the five fungi, while for the middle retention (0.030% m/m) four of the five decay fungi were controlled. In Australia the AS1604-2012 series specifies that timber or engineered wood products treated to Hazard Class 3 shall contain a minimum total azole retention in the penetration zone of 0.060% m/m, where the total azole retention equals the sum of the respective propiconazole and tebuconazole retentions. The results (mean percentage mass loss) in Table 8 show that the azole-containing preservative formulated in a low aromatic hydrocarbon carrier is highly efficacious, with all five decay fungi controlled (mass loss <3%) at the 0.060% m/m retention.

Example 8

Figure 7:
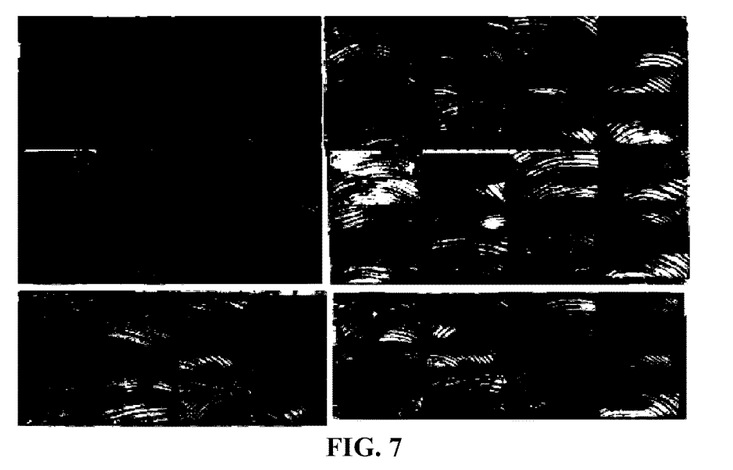
FIG. 7 relates to Example 8. Shown are images of freshly cut ends of samples treated with a low odour/low aromatic wood preservative containing tebuconazole, propiconazole, permethrin and copper naphthenate (present as a penetration marker), taken after spraying with PAN indicator.

In this Example the treatment of *pinus radiata* with a low odour/low aromatic wood preservative formulation is investigated. Extensive treatment trials have been carried out with end-sealed *radiata* pine samples of various end-sections. These samples were treated with a low odour/low aromatic (<1.0% w/v aromatics) formulation containing 4.5 g/L of tebuconazole, 4.5 g/L propiconazole and 3.3 g/L permethrin. The formulation also contained 10 g/L of copper naphthenate (6% w/w copper metal) as a penetration marker. The samples were weighed before and after treatment to determine preservative uptake. Several days after treatment, the specimens were cut and penetration assessed after spraying cut ends with PAN indicator (AWPA A3-08; Method 14). The penetration results are shown in FIG. 7.

Two adjacent sections were cut from various samples that were considered to be adequately treated based on the results of a spot test. The sections were analysed for the active ingredients tebuconazole, propiconazole and permethrin. One section was used to analyse the full cross-section, the second section was used to analyse the inner one-ninth (or core) of the samples. Some of the results are summarised in Table 9.

TABLE 9

Summary of results for Example 8

| Sample | Uptake (L/m³) | Full cross section (% m/m) | | | Inner one-ninth (% m/m) | | |
|---|---|---|---|---|---|---|---|
| | | Teb | Prop | Perm | Teb | Prop | Perm |
| 1 | 39.0 | 0.057 | 0.043 | 0.036 | 0.035 | 0.033 | 0.025 |
| 2 | 39.0 | 0.050 | 0.044 | 0.031 | 0.030 | 0.030 | 0.023 |
| 3 | 39.0 | 0.061 | 0.055 | 0.036 | 0.033 | 0.030 | 0.021 |
| 4 | 41.6 | 0.063 | 0.063 | 0.042 | 0.033 | 0.033 | 0.026 |

The samples all contain >0.06% m/m total azole (tebuconazole/propiconazole) and >0.02% m/m permethrin in the full cross-section, as expected on the basis of piece uptakes recorded for individual samples. The inner one-ninth analyses revealed that, on average, 59% of the full cross-section retention was found in the core, demonstrating the ease with which the low odour/low aromatic formulations are able to penetrate species such as *radiata* pine.

Example 9

In this Example, the treatment of *pinus pinaster* (maritime pine) with a low odour/low aromatic wood preservative formulation was investigated. End-sealed *pinaster* samples (90×35 mm end section) were treated with a low odour Vacsol Azure formulation containing 4.5 g/L of tebuconazole, 4.5 g/L propiconazole and 3.3 g/L permethrin, where the aromatic content of the formulation was less than 1% w/v. The formulation also contained 10 g/L of copper naphthenate (6% w/w copper metal) as a penetration marker. The samples were weighed before and after treatment to determine preservative uptake. Several days after treatment the specimens were cut and penetration assessed after spraying cut ends with PAN indicator (AWPA A3-08; Method 14). The results of treatment are summarised in Table 10.

Figure 8:
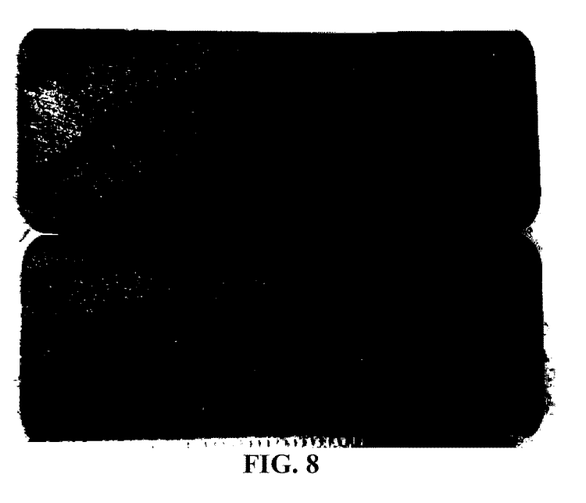
FIG. 8 relates to Example 9. Shown are end-sections of *Pinaster* pine Samples 1 (top) and 2 (bottom) after treatment with low odour/low aromatic solvent-based preservative and application of PAN indicator to cut ends.

The sapwood of each of the samples was penetrated fully, as judged by the colour development on the end-grain upon application of the PAN indicator (see, e.g., FIG. 8). Samples 3 and 4 were typical of high density *pinaster* pine, with 5-7 growth rings/10 mm. The sapwood was penetrated fully, and the envelope on the heartwood was sufficient to meet the penetration requirements of AS1604.1-2012.

TABLE 10

Treatment of pinaster pine with low odour/low aromatic wood preservative formulation

| Sample Number | Density (kg/m³)[a] | Heartwood (%)[b] | Blue-stain[c] | Uptake (L/m³)[d] | Sapwood penetration (%)[e] | Heartwood penetration (P/F)[f] |
|---|---|---|---|---|---|---|
| 1 | 517 | 0 | N | 36.0 | 100 | N/a |
| 2 | 478 | 0 | Y | 38.6 | 100 | N/a |
| 3 | 584 | 70 | N | 34.8 | 100 | P |
| 4 | 615 | 80 | N | 33.2 | 100 | P |

[a]Density
[b]Heartwood content determined by spot test; AS/NZS1605.1:2006.
[c]Visual detection of blue-stain (Y = yes, N = no).
[d]Uptake determined by weighing samples before and after treatment.
[e]AWPA A3-08; Method 14.
[f]Pass (P) or Fail (F) as judged by penetration criteria in AS1604.1-2013 for Hazard Class 3

Figure 9:
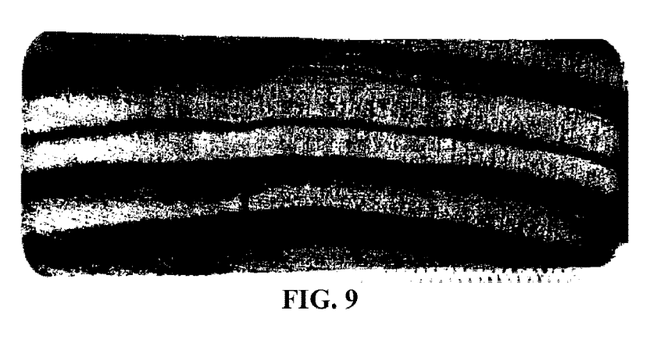
FIG. 9 relates to Example 9. Shown is the end-section of *Pinaster* pine Sample 2 showing presence of blue-stain, prior to treatment with a low odour/low aromatic solvent-based preservative.

Sample 2 was a lower density sample that was free of heartwood. Although blue-stain was readily visible in this sample (see, FIG. 9), the uptake was not appreciably different to that for Sample 1; this finding was surprising. The presence of sapstain or blue-stain in kiln-dried timber frequently gives rise to increased uptakes upon preservative treatment, especially when treating with light organic solvent-based preservatives where increases in uptake of up to 100% are regularly seen, that cannot be reduced even with extended vacuum schedules. Hence, the presence of blue-stain gives rise to increased treatment costs. It would appear that the low aromatic carrier is less susceptible to exhibiting high uptakes when blue-stain is present in the substrate.

Example 10

In this Example, the influence of carrier on uptake in sapstained timber is investigated. As discussed above, the presence of sapstain or blue-stain in kiln-dried timber frequently gives rise to increased uptakes upon preservative treatment. In a further trial investigating the treatability of *radiata* pine with a low odour, solvent-based formulation, blue-stain was visibly present in a number of the samples. Upon treatment with a low odour solvent-based formulation it was found that uptakes were only slightly higher than may have been expected, with charges uptakes in the range 46-49 L/m³ over several end-sections (90×35 mm, 90×45 mm and 140×45 mm). What was surprising was the absence of very high uptakes that are typically observed when blue-stain is present, resulting in charge uptakes that are substantially higher than normal. In blue-stain free samples, uptakes were in the range 42-45 L/m³ for the same end-sections.

Example 11

In this Example, the influence of carrier on treatment of different end-sections was investigated. When treating structural timber with light organic solvent preservatives it is often observed that using the same schedule on different end-sections results in different mean uptakes, and as a consequence different penetration patterns. For example, treatment of a particular *radiata* pine resource of 90×35 mm end-section with Vacsol® Azure C (that uses a traditional kerosene carrier containing approximately 17% aromatics) using a modified Lowry process (+50 kPa/40 sec; −90 kPa/15 min) resulted in a mean uptake of 40.4 L/m³ (and satisfactory penetration), whereas the same schedule on 140×45 mm end-section *radiata* pine gave a mean uptake of 33.5 L/m³, and unsatisfactory penetration.

Satisfactory penetration of the 140×45 mm end-section was achieved with a heavier schedule delivering a mean uptake of 43 L/m³. The implications are that if the mixed end-sections are treated in the same charge, either (i) unsatisfactory treatment quality for the larger end-section will result, or (ii) the smaller end-section will be over-treated. Treatment quality and preservative consumption may be optimised by treating the different end-sections in different charges, however may not always possible. For example, when insufficient timber of a particular end-section is available to make a full charge the efficiency of the plant decreases, which is also undesirable.

An additional feature of the low odour/low aromatic wood preservative formulation is that different end-sections of the same *radiata* pine resource gave relatively consistent uptakes. The results are summarised in Table 11. In this trial a formulation containing the active ingredients tebuconazole, propiconazole and permethrin formulated in a low aromatic carrier (<1.0% w/v aromatics) was used to treat end-sealed *radiata* pine samples of different end-section, sourced from the same mill. The same treatment schedule was used in each case, and the uptakes were similar across the three end-sections.

TABLE 11

Treatment of radiata pine with a low odour/low aromatic wood preservative formulation

| End-section (mm) | Mean uptake (L/m³)ᵃ |
|---|---|
| 90 × 35 | 47.5 |
| 90 × 45 | 47.1 |
| 140 × 45 | 47.4 |

ᵃMean of 20 boards for 90 × 35 and 140 × 45 mm, and 30 boards for 90 × 45 mm

Example 12

In this Example, the influence of the carrier on the penetration of heartwood was examined. An additional unexpected benefit of the low odour/low aromatic wood preservative was the improvement in penetration of *radiata* pine heartwood. Light organic solvent preservatives typically treat *radiata* pine sapwood somewhat inconsistently, in that samples with heartwood typically display lower uptakes than those without heartwood. Envelope penetration on heartwood is sometimes observed, but it can be inconsistent.

End-sealed *radiata* pine samples either 90×45 or 140×45 mm in end-section, that contained various amounts of heartwood were treated with the low odour/low aromatic formulation used in Example A4. After airing the specimens they were cut and penetration assessed via PAN spot test indicator. The preservative penetration in the heartwood containing samples was surprisingly good, with at least 90% of the heartwood penetrated, as judged by positive response to the spot test indicator.

TABLE 12

Treatment of radiata pine with low odour/low aromatic wood preservative formulation

| End-section (mm) | Heartwood content (%) | Piece uptake (L/m³) | Preservative penetration |
|---|---|---|---|
| 90 × 45 | 50 | 42.0 | 100 |
| 140 × 45 | 25 | 48.7 | 90 |
| 140 × 45 | 20 | 40.9 | 90 |

TABLE 12-continued

Treatment of radiata pine with low odour/low aromatic wood preservative formulation

| End-section (mm) | Heartwood content (%) | Piece uptake (L/m³) | Preservative penetration |
|---|---|---|---|
| 140 × 45 | 25 | 45.5 | 100 |
| 140 × 45 | 25 | 49.4 | >95 |

Reference throughout this specification to "one embodiment" or "an embodiment" means that a particular feature, structure or characteristic described in connection with the embodiment is included in at least one embodiment of the present invention. Furthermore, the particular features, structures or characteristics may be combined in any suitable manner, as would be apparent to one of ordinary skill in the art from this disclosure, in one or more embodiments.

In the description provided above, while there has been described what are believed to be the preferred embodiments of the invention, those skilled in the art will recognise that other and further modifications may be made thereto without departing from the spirit of the invention, and it is intended to claim all such changes and modifications as fall within the scope of the invention. For example, any formulas given above are merely representative of procedures that may be used. Steps may be added or deleted to methods described within the scope of the present invention.

It will be appreciated that the above-described invention provides for a low aromatic, or substantially low aromatic solvent carrier for a wood preservative formulation, wherein the carrier provides for efficacious penetration of the preservative into the wood—but does not bear the undesirable odour, toxicity and environmental disbenefits that characterise the more "traditional" LOSP solvent carriers such as mineral spirits, kerosene and diesel.

The prior art is characterised by the use of odoriferous solvent carriers for use in timber preservative formulations; the present invention addresses some of the drawbacks relating to the issue of odour.

The claims defining the invention are as follows:

1. A preservative formulation for use in treating wood or other cellulosic formulations, the formulation comprising: at least one preservative; and a carrier system, the carrier system comprising one or more low aromatic, or substantially low aromatic solvents, wherein the carrier system comprise an aromatics content of about 15% v/v or less, and wherein the one or more low aromatic, or substantially low aromatic solvents comprises a flash point of equal to or greater than 61° C.

2. A formulation according to claim 1, wherein the low aromatic solvent is selected from the group consisting of dearomatised hydrocarbon fluids, isoparaffinic fluids, and mixtures thereof.

3. A formulation according to claim 1, wherein the low aromatic solvent comprises a dearomatised hydrocarbon solvent having a boiling range of from 150° to 196° C. or from 200° to 250° C.

4. A formulation according to claim 1, comprising two low aromatic solvents in a ratio from about 1:99 to about 99:1 w/w.

5. A formulation according to claim 4, wherein the ratio is about 50:50 w/w.

6. A formulation according to claim 1, wherein the one or more low aromatic solvents comprise an aromatics content of less than about 1% w/v.

7. A formulation according to claim 1, wherein the preservative formulation has an uptake in sapwood of less than about 150 L/m3.

8. A formulation according to claim 1, wherein the preservative formulation has an uptake in sapwood of less than about 50 L/m3.

9. A formulation according to claim 1, further comprising at least one biocidal metal compound.

10. A formulation according to claim 9, wherein the biocidal metal compound is a compound of copper.

11. A formulation according to claim 1, wherein the preservative is selected from the group consisting of: insecticides, termidicides, fungicides, mouldicides, or the like, and mixtures thereof.

12. A formulation according to claim 11, wherein the preservative is a triazole compound of formulae (I) or (II):

wherein R1 represents a branched or straight chain C1-5alkyl group; R2 represents a phenyl group optionally substituted by one or more substituents selected from halogen, C1-3alkyl, C1-3alkoxy, phenyl and nitro; R3 is as defined for R2; and R4 represents a hydrogen atom or a branched or straight chain C1-5alkyl.

13. A formulation according to claim 11, wherein the preservative is a fungicide selected from azaconazole, tebuconazole, propiconazole, cyproconazole, hexaconazole, triadamefon, 4,5-dichloro-2-n-octyl-4-isothiazolin-3-one (DCOIT), didecyldimethylammonium chloride, didecyldimethylammonium carbonate/bicarbonate, benzalkonum chloride, penflufen, 3-iodo-2-propynyl-butylcarbamate (IPBC), copper naphthenate, copper oxine, copper octanoate, copper soaps, zinc naphthenate, zinc octanoate, zinc soaps, tributyltin naphthenate, chlorothalonil, or pentachlorophenol.

14. A formulation according to claim 13, further comprising an insecticide.

15. A formulation according to claim 11, comprising tebuconazole, propiconazole and an insecticide dissolved in a suitable co-solvent, diluted with a low odour solvent containing less than 15% aromatic components.

16. A treated wood that has been treated with the formulation defined in claim 1, wherein the preservative penetration within the treated wood is by way of substantially complete penetration.

17. A treated wood according to claim 16, comprising below about 10% w/w preservative content.

18. A method of treating a substrate of wood or other cellulosic formulation which comprises applying to the substrate a preservative formulation as defined according to claim 1.

19. A method according to claim 18, wherein the step of contacting the wood is performed by means selected from the group consisting of: pressure application, spraying, dipping, rolling, painting, or any combination thereof.

20. A method according to claim 19, further comprising at least one vacuum step.

21. A method according to claim 19, further comprising at least one pressure step.

22. A formulation comprising: tebuconazole, propiconazole and permethrin dissolved in a suitable co-solvent, diluted with a low odour solvent, wherein the low odour solvent comprises an amount of about 15% or less of aromatic components, and an amount of water, wherein a moisture content of timber treated with said formulation remains less than 30% immediately after treatment.

23. A formulation according to claim 22, further comprising at least one of surfactants/emulsifiers, other co-solvents, mouldicides, anti-foam agents, water repellent components, colour additives, adhesion promoters, or penetration marker compounds.

* * * * *